US007455656B2

(12) United States Patent
Langeler et al.

(10) Patent No.: US 7,455,656 B2
(45) Date of Patent: Nov. 25, 2008

(54) PILL DELIVERY SYSTEM

(76) Inventors: Gerard E. Langeler, 150 Cook Hill Rd., Apt. 1207, Woodbridge, CT (US) 06410; Lawrence S. Walters, Jr., 505 Amity Rd., Woodbridge, CT (US) 06525

( * ) Notice: Subject to any disclaimer, the term of this patent is extended or adjusted under 35 U.S.C. 154(b) by 0 days.

(21) Appl. No.: 10/206,134

(22) Filed: Jul. 26, 2002

(65) Prior Publication Data

US 2003/0057115 A1 Mar. 27, 2003

Related U.S. Application Data

(60) Provisional application No. 60/307,963, filed on Jul. 26, 2001.

(51) Int. Cl.
*A61J 7/00* (2006.01)
*A61M 5/178* (2006.01)

(52) U.S. Cl. ............................ 604/78; 604/77; 604/212

(58) Field of Classification Search .............. 604/890.1, 604/500, 514, 518, 58, 59, 60, 93.01, 181, 604/275, 77, 78, 212; 239/238; 426/104, 426/115, 117; 222/205, 207; 215/387
See application file for complete search history.

(56) References Cited

U.S. PATENT DOCUMENTS

| | | | | | |
|---|---|---|---|---|---|
| 4,106,673 | A | * | 8/1978 | Donoghue | 222/207 |
| 4,116,195 | A | * | 9/1978 | James | 604/244 |
| 4,474,312 | A | * | 10/1984 | Donoghue | 222/205 |
| 4,776,494 | A | * | 10/1988 | Holoubek | 222/207 |
| 4,805,811 | A | * | 2/1989 | Wetterlin | 128/203.12 |
| 5,154,325 | A | * | 10/1992 | Ryder et al. | 222/189.06 |
| 5,542,579 | A | * | 8/1996 | Robbins, III | 222/158 |
| 5,681,279 | A | * | 10/1997 | Roper et al. | 604/57 |
| 5,922,349 | A | * | 7/1999 | Elliesen et al. | 424/439 |

* cited by examiner

*Primary Examiner*—Kevin C. Simmons
*Assistant Examiner*—Elizabeth R MacNeill
(74) *Attorney, Agent, or Firm*—Ohlandt, Greeley, Ruggiero & Perle, L.L.P.

(57) ABSTRACT

A convenient pill delivery system comprising a container, a consumable substance contained in such container, and a specialized cap capable of receiving one or more pills. The consumable substance is forced out of the container onto the cap and surrounds and encompasses the pill. The consumer licks the pill and consumable substance together off the cap and swallows it. The consumable substance provides bulk and lubrication to the pill and aids the consumer in swallowing the pill quickly, easily, and efficiently.

15 Claims, 3 Drawing Sheets

PILL DELIVERY SYSTEM

This application claims priority from U.S. Provisional Patent Application No. 60/307,963, filed on Jul. 26, 2001.

The present invention relates generally to an improved pill delivery system and the method for administering the same. More particular, the present invention relates to a drug delivery system that will be used by those patients who have difficulty swallowing pills or who do not have access to food or water during the taking of pills.

BACKGROUND OF THE INVENTION

Oral administration of medicaments, vitamins, food, supplements, and other substances in pill, tablet, and capsule form present special problems to a large segment of the population, especially to children and the elderly. There are many people who cannot swallow a pill and will either refuse to take it or gag while trying to swallow it. The term "pill" is used herein for any orally ingestible formulation in the solid state and includes one or more tablets, capsules, caplets, lozenges and the like, as will be apparent to those skilled in the art. While such essentially solid formulations are to be distinguished from tonics, suspensions, dispersions and other essentially liquid formulations, it will be appreciated that an essentially solid "pill" may have a liquid or semi-solid interior.

The art is filled with numerous methods and devices aimed at cutting, crushing, grinding, or otherwise reducing the size of a pill into smaller particles that are easier to swallow. This process is inefficient, time-consuming, and wasteful. Portions of the medicament may be lost in the process, thereby affecting dosage accuracy and, possibly, drug absorption. Furthermore, some pills, such as time-release medicaments, cannot be cut or crushed as this will affect their designed purpose, and the efficacy of their absorption over defined time intervals. Most of the solutions in the prior art involve altering the size, shape, and/or structure of the pill.

Little comfort is given to those people who have trouble swallowing a pill in its manufactured state. The art is lacking simple, innovative devices or methods for making it easier for these people to swallow a pill without changing the pill's size, shape, and/or structure. The ability to easily consume a pill without the need to cut, crush, grind or otherwise alter its natural state would be efficient, convenient, and readily embraced by all people who have difficulty or find it unpleasant to consume a pill in its manufactured state.

Even for people who do not have trouble swallowing a pill, substances such as food, water, or other fluids are often required to assist in swallowing it. Without such lubrication, the pill may become stuck, lodge in the throat, and cause choking. Food, water, or other fluids may not always be available when a consumer needs or desires to take a pill, and hence, the ability to take a pill without dependence on such substances would be advantageous.

The present invention provides an easy and convenient solution to swallowing a pill without changing the size, shape, or structure of the pill itself. The present invention allows the consumer to easily and conveniently swallow the pill in its manufactured form. This is a unique solution to the problem of swallowing pills and represents a radical departure from the prior art, which essentially teaches the consumer to cut, crush, or otherwise reduce the size of the pill or otherwise change its structure to make it easier to swallow. Furthermore, the present invention enables the consumer to swallow a pill, even at times when access to food or fluids is inconvenient.

SUMMARY OF THE INVENTION

A container filled with a consumable substance that is attached to a specialized top or cap, wherein the cap is uniquely designed to receive one or more pills, tablets, or other objects that the user desires to swallow, preferably without chewing. This consumable substance provides a measure of bulk and lubrication to the pill, which is intended to aid the consumer in overcoming the natural gag reflex. By some applied force, the consumable substance is delivered to the cap and surrounds at least a portion of the pill. The consumer then simply licks the cap and receives the pill, which is now at least partially encompassed in the consumable substance. Once in the mouth, the consumable substance permits the user to more easily and quickly swallow the pill without gagging on or chewing it.

The consumable substance is formulated to break down quickly by the gastric fluids in the stomach so that the pill is readily available for use by the body. The present invention could be manufactured in various sizes and contain correspondingly different volumes of consumable substances, which could also be offered in different flavors and textures. The amount of consumable substance in a given size container will determine the number of administrations available for use in consuming pills.

DETAILED DESCRIPTION OF THE PREFERRED INVENTION

Figure 1:
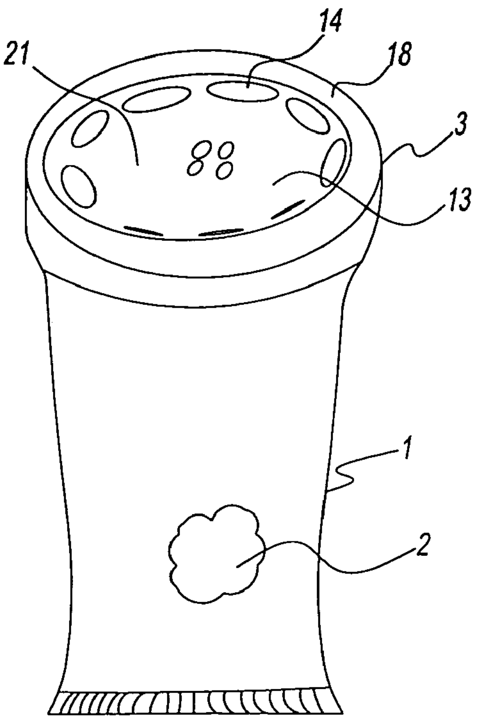
FIG. 1 is a schematic view of the container and cap of the present invention.

The pill delivery system according to the present invention is best illustrated by reference to FIGS. 1-7. Referring to FIG. 1, the present invention is essentially composed of a flexible tube, sleeve, housing, or other container 1, filled with a consumable substance 2, which is delivered by some force onto the cap 3. All materials should be food-grade and approved by the appropriate authorities. Depicted in FIG. 1, the preferred mode for the container would be a thin flexible sleeve 1, similar to a toothpaste tube with the terminal end crimped to seal in the contents. This type of container permits easy access to the contents by squeezing the tube and forcing the contents out onto cap 3. This type of tube is easy to manufacture and serves as a simple, inexpensive means for storing and delivering the contents for use. The dimensions of sleeve 1 will determine the amount of the consumable substance 2 that may be stored inside, and, hence, the number of pill administrations available to the consumer.

Figure 2:
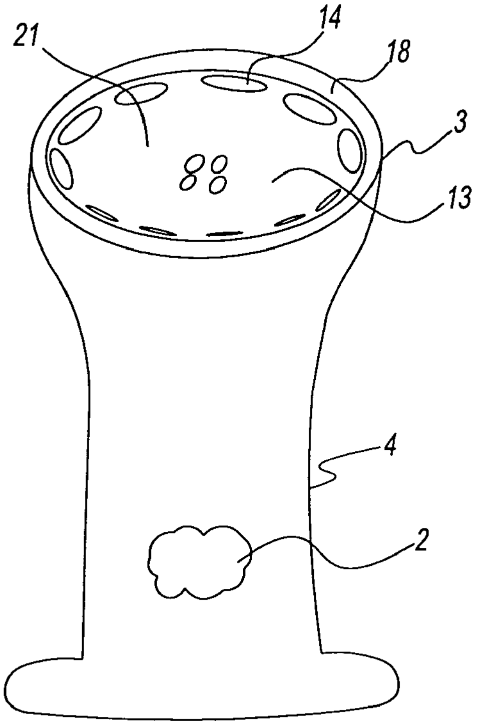
FIG. 2 is a schematic view of the container and cap of the present invention with a squeezable casing.
Figure 3:
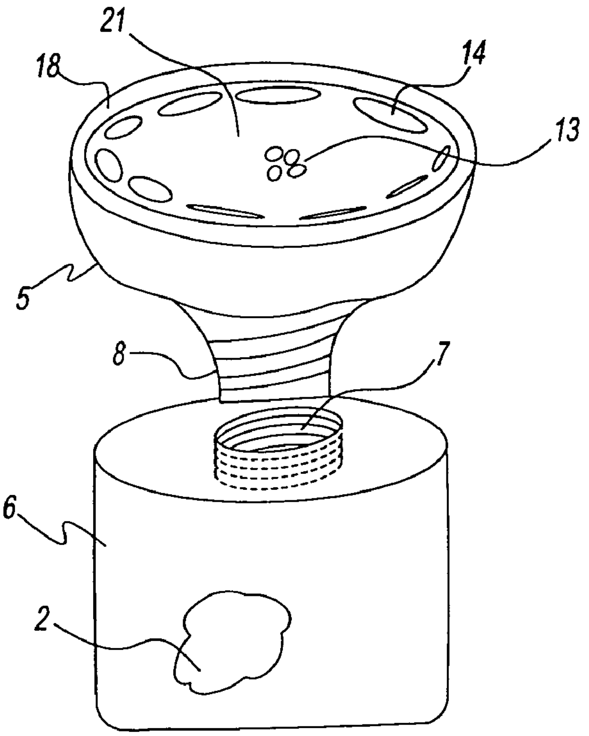
FIG. 3 is a schematic view of the cap of the present invention shown in a replaceable configuration capable of being installed on a refill container.
Figure 4:
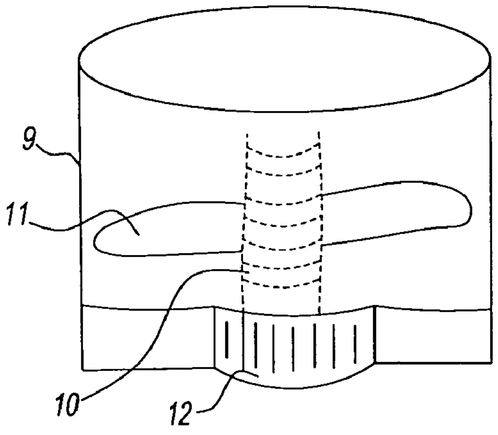
FIG. 4 is a schematic cut-a-way view of the container of the present invention using a knurled wheel with an internal threaded post and platform.

Although squeezing the sleeve is easy and convenient, other containers and means of applying force to deliver contents 2 from sleeve 1 could also be employed. FIG. 2 depicts cap 3 attached to a sturdy, but flexible-sided container 4, which when squeezed, deflects to apply pressure to contents 2, but then returns to its original shape once the pressure is released. FIG. 3 shows cap 5 in a replaceable configuration, capable of being fastened onto new refill container 6, filled with consumable substance 2, at connecting interfaces 7 and 8. FIG. 4 shows new container 9 with an internal threaded post 10 and rising platform 11 driven by knurled wheel 12. When knurled wheel 12 is turned, the attached threaded post 10 raises platform 11 and pushes the contents upward, similar to the operation of commercially available deodorant containers.

The terms tube, sleeve, housing, and container are used interchangeably throughout to refer to the vessel containing the consumable substance. For purposes of this patent, the container, in general, will be referred to as sleeve 1. Although the sleeve is often referred to throughout this patent, it is not intended to limit other possibilities, and other suitable containers may be used, as will be apparent to one skilled in the art.

Consumable substance 2, herein referred to as a "gel", may be formulated from any number of ingredients, the resulting qualities of which would most likely be a viscous substance, resembling a gel or paste, that is slippery in texture, with a low coefficient of friction, and has the properties of flowing under pressure through one or more channels, holes or vents and then, reconsolidating into a uniform mass. The gel must be capable of covering at least a portion of the pill and provides an appropriate amount of bulk and/or lubrication. It may be helpful, but not required, to incorporate a property into the gel that causes the gel to thicken, stiffen, or harden after contact with air. This will cause the gel to provide a fuller or stronger covering to the pill with less chance for the pill to become dislodged from the gel and trigger the consumer's gag reflex. The gel could also be a type of liquid, provided it could contain the necessary properties to cover at least a portion of the pill to enable it to be easily swallowed.

Figure 7:
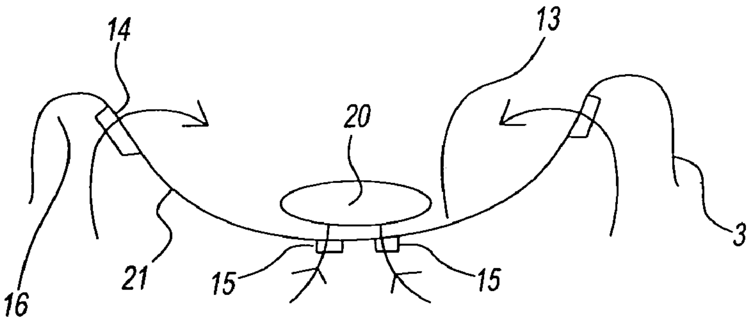
FIG. 7 is a schematic cut-a-way view of the cap of the present invention in operation showing a pill in the concave section of the cap and the consumable substance being pushed out of the vents and surrounding the pill.

Affixed to the open end of sleeve 1, opposite the closed or crimped end, would be a specialized cap 3, as depicted in FIGS. 1-3. Although the cap could be constructed from any firm, resilient material, it would be most preferably made from a food-grade injected molded plastic in the polypropylene or polyethylene family of plastics. The cap might also be manufactured with an antimicrobial or biocidal agent added to the plastic to control viruses, bacteria, and other organisms that may be deposited or grow on the cap or on any remains possibly left on the cap after use. The cap could be manufactured in a variety of configurations, with the top of the cap being flat, raised, or recessed, provided that one or more pills could be placed thereon and the gel could be squeezed or somehow forced to flow around and/or over at least a portion of the pill(s). The most preferred means, as shown in FIGS. 1 and 7, would be to have a concave, recessed cap having a surface 21 resembling a bowl 13 with holes or vents disposed in the surface 21 along the top inside edge of the cap 14 and at the bottom of the cap 15. The surface 21 is continuous between each of the holes or vents. The holes provide a point of exit for the gel to flow out of the sleeve and on to cap 3.

Figure 5:
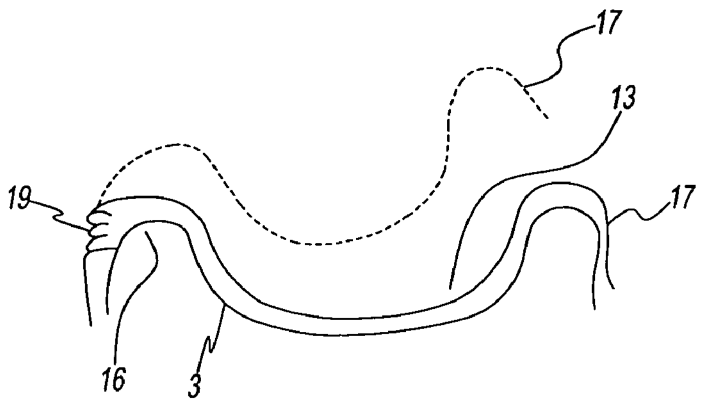
FIG. 5 is a schematic cut-a-way view of the cap of the present invention with a swing-a-way form-fitting cover hinged to the cap.
Figure 6:
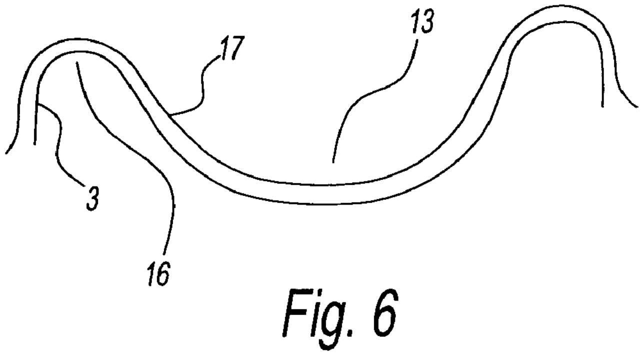
FIG. 6 is a schematic cut-a-way view of the cap of the present invention with a removable form-fitting cover.

The process for using the present invention would be a simple operation that the consumer could perform or it could be performed by a third party, such as a parent for a child or a nurse for a patient. As depicted in FIGS. 1, 5, 6, and 7, the consumer or assistant would remove fitted cover 17, to expose cap 3. As depicted in FIGS. 1 and 6, cover 17 is intended to be a form-fitting cover that interfaces tightly against the entire shape of top 18 and inner portion 13 of cap 3, and would most likely be made from a plastic material. However, cover 17 could even be a paper or other material barrier seal simply covering the top of the cap. Depending on the manufacturer's preference, a form-fitting cover 17 could be optimized to also serve as a tamper-resistant seal, or the open end of sleeve 1 under cap 3 could be additionally sealed with suitably removable tamper-resistant covering for safety and health reasons. In this case, cap 3 would have to be temporarily removed, the safety seal would then also have to be removed, and then cap 3 replaced for before use. As may be apparent to one skilled in the art, cover 17 could be entirely removable, as shown in FIG. 6, or it could be attached to container 1 or cap 3 by an attachment in the nature of a hinge 19, as shown in FIG. 5. Hinge 19 would enable cover 17 to be attached to the side of cap 3, and swung out of the way sufficient for the consumer to use the device without being impeded by cover 17, and then easily replaced when finished. This attachment would also prevent cover 17 from being misplaced while using the device.

The consumer would then place the pill in the concave, bowl section in the top of cap 13, squeeze sleeve 1 until a sufficient amount of gel 2 is delivered around, under and over the pill, as dictated by each consumer—s perference, and then the consumer would lick the pill and surrounding gel off the cap and, perferably, swallow same immediately. If the consumer was not able to swallow the pill on the first try, the entire process could be repeated, or the consumer could squeeze out an additional amount of gel and lick that portion from the cap to provide sufficient quanity of gel in the mouth to mask the pill and enable the consumer to easily swallow it. By experimenting with the device, a consumermat find it helpful to first try the gel without a pill to get acquanited with the taste, texture, and mouth-feel of the gel. Once familiar with the gel, the consumer would load a pill onto the cap and consume it as provided above. Once proficient with the device, an experienced consumer could take more than one pill at one time, making the pill consumption process quicker, more efficient and less expensive per administration. To accomplish this, the consumer would load the desired number of pills onto the cap 3, squeeze out a sufficient amount of gel 2 to cover at least a portion of them, and then simultaneously lick the collection of pills and gel off the cap together. Once finished, cap 3 could then be wiped clean, if nesscessary, and cover 17 replaced until next use. With single serving sizes, the user would simply discard the device after use, and use a new one next time a pill needs to be taken.

While the present invention has been described in combination with embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

What is claimed is:

1. A system for delivering one or more pills which comprises:

a housing having at least a portion that is flexible and containing, said consumable substance is at least one selected from the group consisting of: a gel, a paste, a liquid, and other viscous substances, said housing being closed at one end and opened at the opposite end;

a cap sealingly disposed about said open end, said cap having a surface, said cap having a pill holding region with a concave recessed portion; and a plurality of holes or vents disposed in said surface about an outer circumference of a top inside edge of said cap, in said surface at a bottom of said concave recessed portion of said cap, and in said surface in any region therebetween said top inside edge of said cap and said concave recessed portion of said cap, wherein said plurality of holes or vents place said housing in direct fluid communication with said concave recessed portion of said cap, wherein said consumable substance may pass from said housing into said pill holding region through all of said plurality of holes or vents substantially simultaneously, and wherein said pill holding region is sized and shaped to retain said consumable substance and the one or more pills.

2. The system according to claim 1, wherein said concave recessed portion is disposed on a portion of the surface of said cap away from said housing and wherein said plurality of holes or vents transport said consumable substance so as to surround the one or more pills.

3. The system according to claim 1, wherein said housing is a flexible tube.

4. The system according to claim 1, wherein said cap includes a cover portion.

5. The system according to claim 4, wherein said cover portion is hingeably connected to said cap.

6. The system according to claim 1, wherein said cap is formed from a material selected from the group consisting of: plastic, polypropylene, polyethylene, and a resilient material.

7. The system according to claim 1, wherein said cap includes either an antimicrobial or biocidal agent.

8. The system according to claim 1, wherein said surface is continuous between said plurality of holes or vents.

9. A pill delivery container which comprises: a housing that is closed at one end and opened at an opposite end; a cap sealingly disposed about said open end, said cap having a surface, said a cap having a pill holding region and a means for transporting said comsumable substance is at least one selected from the group consisting of: a gel, a paste, a liquid, and other viscous substances; from said housing to said cap, said pill holding region being a concave recessed portion having a plurality of holes or vents disposed in said surface about an outer circumference of a top inside edge of said cap, in said surface at bottom of said concave recessed portion of said cap, and in said surface in any region therebetween said top inside edge of said cap and said concave recessed portion of said cap, wherein said plurality of holes or vents place said housing in direct fluid communication with said concave recessed portion of said cap, wherein said housing comprises at least a flexible portion so that actuation of said flexible portion causes flow of said consumable substance along said means for transporting from said housing through all of said plurality of holes or vents substantially simultaneously and into said pill holding region.

10. The container according to claim 9, wherein said cap includes a cover portion.

11. The system according to claim 10, wherein said cover portion is hingeably connected to said cap.

12. The container according to claim 9, wherein said cap is formed from a material selected from the group consisting of: plastic, polypropylene, polyethylene, and a resilient material.

13. The system according to claim 9, wherein said cap includes comprises either an antimicrobial or biocidal agent.

14. The container according to claim 9, wherein said surface is continous between said plurality of holes or vents.

15. A system for delivering one or pills which comprises:

a housing having a closed end, at least one flexible portion, and a open end, said housing being configured to store said consumable substance is at least one selected from the group consisting of: a gel, a paste, a liquid, and other viscous substances; and a cap sealingly disposed about said open end, said cap having a surface, said cap comprising a concave recessed portion and a plurality of holes or vents disposed in said surface about an outer circumference of a top inside edge of said cap, in said surface at a bottom of said concave recessed portion of said cap, and in said surface in any region therebetween said top edge of said cap and said concave recessed portion of said cap, wherein said plurality of holes or vents place said housing in direct fluid communication with said concave recessed portion of said cap, and wherein said concave recessed portion of said cap has a depth sufficient to receive said consumable substance and the one or more pills so that a human can simultaneously lick said consumable substance and the one or more pills from said concave recessed portion of said cap.

* * * * *